US008012699B2

(12) United States Patent
Ching

(10) Patent No.: US 8,012,699 B2
(45) Date of Patent: Sep. 6, 2011

(54) RECOMBINANT ANTIGENS FOR DIAGNOSIS AND PREVENTION OF MURINE TYPHUS

(75) Inventor: Wei-Mei Ching, Bethesda, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 30 days.

(21) Appl. No.: 12/454,038

(22) Filed: Apr. 27, 2009

(65) Prior Publication Data

US 2010/0311088 A1 Dec. 9, 2010

Related U.S. Application Data

(62) Division of application No. 11/789,122, filed on Apr. 18, 2007, now Pat. No. 7,544,778.

(60) Provisional application No. 60/793,583, filed on Apr. 20, 2006.

(51) Int. Cl.
*G01N 33/53* (2006.01)
*G01N 33/569* (2006.01)

(52) U.S. Cl. .......................... 435/7.1; 435/7.2; 435/7.32

(58) Field of Classification Search ........................ None
See application file for complete search history.

(56) References Cited

U.S. PATENT DOCUMENTS 5,783,441 A 7/1998 Carl et al.
2004/0053216 A1 * 3/2004 Hooper et al. .................... 435/5

OTHER PUBLICATIONS

Hahn, et al, Cloning and Sequence Analysis of the Gene Encoding the Crystalline Surface Layer Protein of Rickettsia typhi, 1993, vol. 133, pp. 129-133.

* cited by examiner

*Primary Examiner* — Albert Navarro
(74) *Attorney, Agent, or Firm* — Nina Yang; Albert M. Churillo; Joseph K. Hemby

(57) ABSTRACT

The invention relates to the construction of recombinant, immunodominant *Rickettsia typhi* proteins. The invention also relates to a method for the use of the recombinant proteins, either singly or in combination, in detection and diagnostic assays. The proteins can also be used in anti-*Rickettsia typhi* immunogenic formulations.

5 Claims, 2 Drawing Sheets

Open reading frame of OmpB from R. typhi

Signal peptide β-peptide
1 32 1353 1645

Matured OmpB (a.a. 33-1353)

Frag. A (a.a. 33-274)

Frag. K (a.a. 746-1353)

Frag. AN (aa. 33 to 742

Lane 1. 0.03 μg of OmpA and OmpB proteins of R. r.
Lane 2. 0.1 μg of recombinant chimeric OmpAB protein of R. r.
Lane 3. 0.03 μg of recombinant K fragment of OmpB protein of R. t.

Panel A. Rickettsiae universal negative control serum
Panel B. R. rickettsii positive serum
Panel C. R. prowazekii positive serum
Panel D. R. typhi positive serum

SEQUENCE LISTING

```
<160> NUMBER OF SEQ ID NOS: 12

<210> SEQ ID NO 1
<211> LENGTH: 726
<212> TYPE: DNA
<213> ORGANISM: Rickettsia typhi

<400> SEQUENCE: 1

atgggtgctg ttatgcaata taatagaaca acaaatgcag cagctacaac tgttgatggt      60

gcaggatttg atcaaactgg cgctggtgtt aatcttcctg tcgctacaaa ttcggttatt     120
```

-continued actgctaatt ctaataatgc tattactttt aatactccaa acggtaattt aaatagtttg 180
tttttggata ctgcaaatac tttagcagta acaattaatg aaaatactac cttagggttt 240
gtaactaatg ttactaaaca gggtaacttc tttaatttta ctattggtgc tggtaaaagt 300
cttaccataa caggtcatgg tattactgct caacaagctg ctactacaaa aagtgctcaa 360
aatgttgttt caaaagttaa tgctggtgct gctattaacg ataatgatct tagcggtgta 420
ggatcaatag actttactgc tgcgccttct gtattagaat ttaatttaat aaatcctaca 480
actcaagaag ctcctcttac acttggtgat aatgctaaaa tagttaatgg tgctaatggg 540
atattaaata ttactaatgg gtttgttaag gtttcagata aaacttttgc tggtattaag 600
acaattaata tcggtgataa tcaaggttta atgtttaata ctactcctga tgccgctaat 660
gctttaaatt tgcaaggagg tggtaatact attaatttta atggaagaga cggtactggt 720
aaataa 726

<210> SEQ ID NO 2
<211> LENGTH: 240
<212> TYPE: PRT
<213> ORGANISM: Rickettsia typhi

<400> SEQUENCE: 2

Met Gly Ala Val Met Gln Tyr Asn Arg Thr Thr Asn Ala Ala Ala Thr
1               5                   10                  15

Thr Val Asp Gly Ala Gly Phe Asp Gln Thr Gly Ala Gly Val Asn Leu
            20                  25                  30

Pro Val Ala Thr Asn Ser Val Ile Thr Ala Asn Ser Asn Asn Ala Ile
        35                  40                  45

Thr Phe Asn Thr Pro Asn Gly Asn Leu Asn Ser Leu Phe Leu Asp Thr
    50                  55                  60

Ala Asn Thr Leu Ala Val Thr Ile Asn Glu Asn Thr Thr Leu Gly Phe
65                  70                  75                  80

Val Thr Asn Val Thr Lys Gln Gly Asn Phe Phe Asn Phe Thr Ile Gly
                85                  90                  95

Ala Gly Lys Ser Leu Thr Ile Thr Gly His Gly Ile Thr Ala Gln Gln
            100                 105                 110

Ala Ala Thr Thr Lys Ser Ala Gln Asn Val Val Ser Lys Val Asn Ala
        115                 120                 125

Gly Ala Ala Ile Asn Asp Asn Asp Leu Ser Gly Val Gly Ser Ile Asp
    130                 135                 140

Phe Thr Ala Ala Pro Ser Val Leu Glu Phe Asn Leu Ile Asn Pro Thr
145                 150                 155                 160

Thr Gln Glu Ala Pro Leu Thr Leu Gly Asp Asn Ala Lys Ile Val Asn
                165                 170                 175

Gly Ala Asn Gly Ile Leu Asn Ile Thr Asn Gly Phe Val Lys Val Ser
            180                 185                 190

Asp Lys Thr Phe Ala Gly Ile Lys Thr Ile Asn Ile Gly Asp Asn Gln
        195                 200                 205

Gly Leu Met Phe Asn Thr Thr Pro Asp Ala Ala Asn Ala Leu Asn Leu
    210                 215                 220

Gln Gly Gly Gly Asn Thr Ile Asn Phe Asn Gly Arg Asp Gly Thr Gly
225                 230                 235                 240

<210> SEQ ID NO 3
<211> LENGTH: 1863
<212> TYPE: DNA
<213> ORGANISM: Rickettsia typhi

<400> SEQUENCE: 3

```
atgtctggtg gaaccagtat agtaagtggt acagttggtg gacagcaagg tcttaagctt     60
aataatttaa tattagataa tggtactact gttaagtttt taggtgatat cacatttaat    120
ggtggtacta aaattgaagg taaatctatc ttgcaaatta gcagcaatta tattactgat    180
catattgaat ctgctgataa tactggtaca ttagaatttg ttaatactga tcctatcacc    240
gtaacgttaa ataaacaagg tgcttatttt ggtgttttaa aacaagtaat ggtttctggt    300
ccaggtaaca tagcatttaa tgagataggt aatggagttg cacatgctat agcagttgat    360
tccatttctt ttgaaaatgc aagtttaggt gcatctttat tcttacttag tggcactcca    420
ttagatgtgc taacaattaa aagtaccgta ggtaatggta cagtagataa ttttaatgct    480
cctattttag ttgtatcagg tattgatagt atgatcaata acggtcaagt tatcggtgat    540
caaaagaata ttatagctct atcgcttgga agtgataaca gtattactgt taattctaat    600
acattatatg caggtatcag aactactaaa actaatcaag gtactgttac acttagcggt    660
ggtataccta ataaccctgg tacaatttat ggtttaggtt tagagaatgg tgatccaaag    720
ttaaagcaag taacgtttac tacagattat aacaacttag gtagtattat tgcaactaac    780
gtaacaatta atgacgatgt aacacttact acaggaggta tagccgggac agattttgac    840
ggtaaaatta ctcttggaag tattaacggt aatgctaatg taaagtttgt tgacagaaca    900
ttttctcatc ctacaagtat gattgtttct actaaagcta atcagggtac tgtaacttat    960
ttaggtaatg cattagtcgg taatattggt agttcagata ttcctgtagc ttctgttaga   1020
tttactggta atgatagtgg tgtaggatta caaggcaata ttcactcaca aaatatagac   1080
tttggtactt ataacttaac tattttaaat tctgatgtaa ttttaggcgg tggtactact   1140
gctattaatg gtgagattga tcttttgaca aataatttaa tatttgcaaa tggtacttca   1200
acatggggca ataatacctc tcttagtaca acattaaacg tatcaaacgg taatgtaggt   1260
caaatagtta ttgctgaagg tgctcaagtt aatgcaacaa ctacaggaac tacaaccatt   1320
aaaatacaag ataatgctaa tgcaaatttc agtggtacac aaacttatac tttaatccaa   1380
ggtggtgcca gatttaacgg tactttagga gctcctaact ttgatgtaac aggaaataat   1440
attttcgtaa aatatgaatt aatacgtgat gcgaatcagg attatgtgtt aacacgtact   1500
aacgatgtat taaatgtagt tacaacagct gtaggaaata gtgcaattgc aaatgcacct   1560
ggtgtacatc aaaatattgc tatatgctta gaatcaactg atacagcagc ttataataat   1620
atgcttttag ctaaagattc ttctgatgtc gcaacattta taggagctat tgctacagat   1680
acaggtgctg ctgtagctac agtaaactta aatgatacac aaaaaactca agatctactt   1740
ggtaataggc taggtgcact tagatatcta agtaattctg aaactgctga tgttggtgga   1800
tctgaaacag gtgcagtatc ttcaggtgat gaagcgattg atcaagtatc ttatggtgta   1860
taa                                                                 1863
```

<210> SEQ ID NO 4
<211> LENGTH: 607
<212> TYPE: PRT
<213> ORGANISM: Rickettsia typhi

<400> SEQUENCE: 4

```
Met Ser Gly Gly Thr Ser Ile Val Ser Gly Thr Val Gly Gly Gln Gln
1               5                   10                  15

Gly Leu Lys Leu Asn Asn Leu Ile Leu Asp Asn Gly Thr Thr Val Lys
            20                  25                  30
```

-continued

```
Phe Leu Gly Asp Ile Thr Phe Asn Gly Gly Thr Lys Ile Glu Gly Lys
        35                  40                  45

Ser Ile Leu Gln Ile Ser Ser Asn Tyr Ile Thr Asp His Ile Glu Ser
    50                  55                  60

Ala Asp Asn Thr Gly Thr Leu Glu Phe Val Asn Thr Asp Pro Ile Thr
65                  70                  75                  80

Val Thr Leu Asn Lys Gln Gly Ala Tyr Phe Gly Val Leu Lys Gln Val
                85                  90                  95

Met Val Ser Gly Pro Gly Asn Ile Ala Phe Asn Glu Ile Gly Asn Gly
            100                 105                 110

Val Ala His Ala Ile Ala Val Asp Ser Ile Ser Phe Glu Asn Ala Ser
        115                 120                 125

Leu Gly Ala Ser Leu Phe Leu Leu Ser Gly Thr Pro Leu Asp Val Leu
    130                 135                 140

Thr Ile Lys Ser Thr Val Gly Asn Gly Thr Val Asp Asn Phe Asn Ala
145                 150                 155                 160

Pro Ile Leu Val Val Ser Gly Ile Asp Ser Met Ile Asn Asn Gly Gln
                165                 170                 175

Val Ile Gly Asp Gln Lys Asn Ile Ile Ala Leu Ser Leu Gly Ser Asp
            180                 185                 190

Asn Ser Ile Thr Val Asn Ser Asn Thr Leu Tyr Ala Gly Ile Arg Thr
        195                 200                 205

Thr Lys Thr Asn Gln Gly Thr Val Thr Leu Ser Gly Gly Ile Pro Asn
    210                 215                 220

Asn Pro Gly Thr Ile Tyr Gly Leu Gly Leu Glu Asn Gly Asp Pro Lys
225                 230                 235                 240

Leu Lys Gln Val Thr Phe Thr Thr Asp Tyr Asn Asn Leu Gly Ser Ile
                245                 250                 255

Ile Ala Thr Asn Val Thr Ile Asn Asp Asp Val Thr Leu Thr Thr Gly
            260                 265                 270

Gly Ile Ala Gly Thr Asp Phe Asp Gly Lys Ile Thr Leu Gly Ser Ile
        275                 280                 285

Asn Gly Asn Ala Asn Val Lys Phe Val Asp Arg Thr Phe Ser His Pro
    290                 295                 300

Thr Ser Met Ile Val Ser Thr Lys Ala Asn Gln Gly Thr Val Thr Tyr
305                 310                 315                 320

Leu Gly Asn Ala Leu Val Gly Asn Ile Gly Ser Ser Asp Ile Pro Val
                325                 330                 335

Ala Ser Val Arg Phe Thr Gly Asn Asp Ser Gly Val Gly Leu Gln Gly
            340                 345                 350

Asn Ile His Ser Gln Asn Ile Asp Phe Gly Thr Tyr Asn Leu Thr Ile
        355                 360                 365

Leu Asn Ser Asp Val Ile Leu Gly Gly Gly Thr Thr Ala Ile Asn Gly
    370                 375                 380

Glu Ile Asp Leu Leu Thr Asn Asn Leu Ile Phe Ala Asn Gly Thr Ser
385                 390                 395                 400

Thr Trp Gly Asn Asn Thr Ser Leu Ser Thr Thr Leu Asn Val Ser Asn
                405                 410                 415

Gly Asn Val Gly Gln Ile Val Ile Ala Glu Gly Ala Gln Val Asn Ala
            420                 425                 430

Thr Thr Thr Gly Thr Thr Thr Ile Lys Ile Gln Asp Asn Ala Asn Ala
        435                 440                 445

Asn Phe Ser Gly Thr Gln Thr Tyr Thr Leu Ile Gln Gly Gly Ala Arg
```

-continued

```
    450                 455                 460

Phe Asn Gly Thr Leu Gly Ala Pro Asn Phe Asp Val Thr Gly Asn Asn
465                 470                 475                 480

Ile Phe Val Lys Tyr Glu Leu Ile Arg Asp Ala Asn Gln Asp Tyr Val
                485                 490                 495

Leu Thr Arg Thr Asn Asp Val Leu Asn Val Val Thr Thr Ala Val Gly
            500                 505                 510

Asn Ser Ala Ile Ala Asn Ala Pro Gly Val His Gln Asn Ile Ala Ile
        515                 520                 525

Cys Leu Glu Ser Thr Asp Thr Ala Ala Tyr Asn Asn Met Leu Leu Ala
    530                 535                 540

Lys Asp Ser Ser Asp Val Ala Thr Phe Ile Gly Ala Ile Ala Thr Asp
545                 550                 555                 560

Thr Gly Ala Ala Val Ala Thr Val Asn Leu Asn Asp Thr Gln Lys Thr
                565                 570                 575

Gln Asp Leu Leu Gly Asn Arg Leu Gly Ala Leu Arg Tyr Leu Ser Asn
            580                 585                 590

Ser Glu Thr Ala Asp Val Gly Gly Ser Glu Thr Gly Ala Val Ser
        595                 600                 605


<210> SEQ ID NO 5
<211> LENGTH: 39
<212> TYPE: DNA
<213> ORGANISM: Rickettsia typhi

<400> SEQUENCE: 5

tctggtgtac atatgggtgc tgtctatgca atataatag                           39


<210> SEQ ID NO 6
<211> LENGTH: 45
<212> TYPE: DNA
<213> ORGANISM: Rickettsia typhi

<400> SEQUENCE: 6

actgacggat ccttattaac cagtaccgtc tcattccatt aaaat                    45


<210> SEQ ID NO 7
<211> LENGTH: 44
<212> TYPE: DNA
<213> ORGANISM: Rickettsia typhi

<400> SEQUENCE: 7

tctttacacc atatgtctgg tggataccaa gtatagtaag tggt                     44


<210> SEQ ID NO 8
<211> LENGTH: 42
<212> TYPE: DNA
<213> ORGANISM: Rickettsia typhi

<400> SEQUENCE: 8

cgcttcggat ccttaagata ctgcacctgt ttcagatcca cc                       42


<210> SEQ ID NO 9
<211> LENGTH: 709
<212> TYPE: PRT
<213> ORGANISM: Rickettsia typhi

<400> SEQUENCE: 9

Met Gly Ala Val Met Gln Tyr Asn Arg Thr Thr Asn Ala Ala Ala Thr
1               5                   10                  15
```

```
Thr Val Asp Gly Ala Gly Phe Asp Gln Thr Gly Ala Gly Val Asn Leu
            20                  25                  30

Pro Val Ala Thr Asn Ser Val Ile Thr Ala Asn Ser Asn Asn Ala Ile
        35                  40                  45

Thr Phe Asn Thr Pro Asn Gly Asn Leu Asn Ser Leu Phe Leu Asp Thr
    50                  55                  60

Ala Asn Thr Leu Ala Val Thr Ile Asn Glu Asn Thr Thr Leu Gly Phe
65                  70                  75                  80

Val Thr Asn Val Thr Lys Gln Gly Asn Phe Phe Asn Phe Thr Ile Gly
                85                  90                  95

Ala Gly Lys Ser Leu Thr Ile Thr Gly His Gly Ile Thr Ala Gln Gln
            100                 105                 110

Ala Ala Thr Thr Lys Ser Ala Gln Asn Val Val Ser Lys Val Asn Ala
        115                 120                 125

Gly Ala Ala Ile Asn Asp Asn Asp Leu Ser Gly Val Gly Ser Ile Asp
    130                 135                 140

Phe Thr Ala Ala Pro Ser Val Leu Glu Phe Asn Leu Ile Asn Pro Thr
145                 150                 155                 160

Thr Gln Glu Ala Pro Leu Thr Leu Gly Asp Asn Ala Lys Ile Val Asn
                165                 170                 175

Gly Ala Asn Gly Ile Leu Asn Ile Thr Asn Gly Phe Val Lys Val Ser
            180                 185                 190

Asp Lys Thr Phe Ala Gly Ile Lys Thr Ile Asn Ile Gly Asp Asn Gln
        195                 200                 205

Gly Leu Met Phe Asn Thr Thr Pro Asp Ala Ala Asn Ala Leu Asn Leu
    210                 215                 220

Gln Gly Gly Gly Asn Thr Ile Asn Phe Asn Gly Arg Asp Gly Thr Gly
225                 230                 235                 240

Lys Leu Val Leu Val Ser Lys Asn Gly Asn Ala Thr Glu Phe Asn Val
                245                 250                 255

Thr Gly Ser Leu Gly Gly Asn Leu Lys Gly Val Ile Glu Phe Asp Thr
            260                 265                 270

Thr Ala Ala Ala Gly Lys Leu Ile Ala Asn Gly Gly Ala Ala Asn Ala
        275                 280                 285

Val Ile Gly Thr Asp Asn Gly Ala Gly Arg Ala Ala Gly Phe Ile Val
    290                 295                 300

Ser Val Asp Asn Gly Asn Ala Ala Thr Ile Ser Gly Gln Val Tyr Ala
305                 310                 315                 320

Lys Asp Ile Val Ile Gln Ser Ala Asn Ala Gly Gly Gln Val Thr Phe
                325                 330                 335

Glu His Leu Val Asp Val Gly Leu Gly Gly Lys Thr Asn Phe Lys Thr
            340                 345                 350

Ala Asp Ser Lys Val Ile Ile Thr Glu Asn Ala Ser Phe Gly Ser Thr
        355                 360                 365

Asp Phe Gly Asn Leu Ala Val Gln Ile Val Val Pro Asn Asn Lys Ile
    370                 375                 380

Leu Thr Gly Asn Phe Ile Gly Asp Ala Lys Asn Asn Gly Asn Thr Ala
385                 390                 395                 400

Gly Val Ile Thr Phe Asn Ala Asn Gly Thr Leu Val Ser Gly Asn Thr
                405                 410                 415

Asp Pro Asn Ile Val Val Thr Asn Ile Lys Ala Ile Glu Val Glu Gly
            420                 425                 430

Ala Gly Ile Val Gln Leu Ser Gly Ile His Gly Ala Glu Leu Arg Leu
        435                 440                 445
```

Gly Asn Ala Gly Ser Ile Phe Lys Leu Ala Asp Gly Thr Val Ile Asn
    450                 455                 460

Gly Pro Val Asn Gln Asn Pro Leu Val Asn Asn Asn Ala Leu Ala Ala
465                 470                 475                 480

Gly Ser Ile Gln Leu Asp Gly Ser Ala Ile Ile Thr Gly Asp Ile Gly
                485                 490                 495

Asn Gly Ala Val Asn Ala Ala Leu Gln Asp Ile Thr Leu Ala Asn Asp
            500                 505                 510

Ala Ser Lys Ile Leu Thr Leu Ser Gly Ala Asn Ile Ile Gly Ala Asn
        515                 520                 525

Ala Gly Gly Ala Ile His Phe Gln Ala Asn Gly Gly Thr Ile Gln Leu
    530                 535                 540

Thr Ser Thr Gln Asn Asn Ile Leu Val Asp Phe Asp Leu Asp Val Thr
545                 550                 555                 560

Thr Asp Gln Thr Gly Val Val Asp Ala Ser Ser Leu Thr Asn Asn Gln
                565                 570                 575

Thr Leu Thr Ile Asn Gly Ser Ile Gly Thr Ile Gly Ala Asn Thr Lys
            580                 585                 590

Thr Leu Gly Arg Phe Asn Val Gly Ser Ser Lys Thr Ile Leu Asn Ala
        595                 600                 605

Gly Asp Val Ala Ile Asn Glu Leu Val Met Glu Asn Asp Gly Ser Val
    610                 615                 620

His Leu Thr His Asn Thr Tyr Leu Ile Thr Lys Thr Ile Asn Ala Ala
625                 630                 635                 640

Asn Gln Gly Lys Ile Ile Val Ala Ala Asp Pro Ile Asn Thr Asp Thr
                645                 650                 655

Ala Leu Ala Asp Gly Thr Asn Leu Gly Ser Ala Glu Ser Pro Leu Ser
            660                 665                 670

Asn Ile His Phe Ala Thr Lys Ala Ala Asn Gly Asp Ser Ile Leu His
        675                 680                 685

Ile Gly Lys Gly Val Asn Leu Tyr Ala Asn Asn Ile Thr Thr Thr Asp
    690                 695                 700

Ala Asn Val Gly Ser
705

<210> SEQ ID NO 10
<211> LENGTH: 330
<212> TYPE: PRT
<213> ORGANISM: Rickettsia typhi

<400> SEQUENCE: 10

Met Ala Gln Lys Pro Asn Phe Leu Lys Lys Ile Ile Ser Ala Gly Leu
1               5                   10                  15

Val Thr Ala Ser Thr Ala Thr Ile Val Ala Gly Phe Ser Gly Val Ala
            20                  25                  30

Met Gly Ala Val Met Gln Tyr Asn Arg Thr Thr Asn Ala Ala Ala Thr
        35                  40                  45

Thr Val Asp Gly Ala Gly Phe Asp Gln Thr Gly Ala Gly Val Asn Leu
    50                  55                  60

Pro Val Ala Thr Asn Ser Val Ile Thr Ala Asn Ser Asn Asn Ala Ile
65                  70                  75                  80

Thr Phe Asn Thr Pro Asn Gly Asn Leu Asn Ser Leu Phe Leu Asp Thr
                85                  90                  95

Ala Asn Thr Leu Ala Val Thr Ile Asn Glu Asn Thr Thr Leu Gly Phe
            100                 105                 110

```
Val Thr Asn Val Thr Lys Gln Gly Asn Phe Phe Asn Phe Thr Ile Gly
        115                 120                 125

Ala Gly Lys Ser Leu Thr Ile Thr Gly His Gly Ile Thr Ala Gln Gln
    130                 135                 140

Ala Ala Thr Thr Lys Ser Ala Gln Asn Val Val Ser Lys Val Asn Ala
145                 150                 155                 160

Gly Ala Ala Ile Asn Asp Asn Asp Leu Ser Gly Val Gly Ser Ile Asp
                165                 170                 175

Phe Thr Ala Ala Pro Ser Val Leu Glu Phe Asn Leu Ile Asn Pro Thr
            180                 185                 190

Thr Gln Glu Ala Pro Leu Thr Leu Gly Asp Asn Ala Lys Ile Val Asn
        195                 200                 205

Gly Ala Asn Gly Ile Leu Asn Ile Thr Asn Gly Phe Val Lys Val Ser
    210                 215                 220

Asp Lys Thr Phe Ala Gly Ile Lys Thr Ile Asn Ile Gly Asp Asn Gln
225                 230                 235                 240

Gly Leu Met Phe Asn Thr Thr Pro Asp Ala Ala Asn Ala Leu Asn Leu
                245                 250                 255

Gln Gly Gly Gly Asn Thr Ile Asn Phe Asn Gly Arg Asp Gly Thr Gly
            260                 265                 270

Lys Leu Val Leu Val Ser Lys Asn Gly Asn Ala Thr Glu Phe Asn Val
        275                 280                 285

Thr Gly Ser Leu Gly Gly Asn Leu Lys Gly Val Ile Glu Phe Asp Thr
    290                 295                 300

Thr Ala Ala Ala Gly Lys Leu Ile Ala Asn Gly Gly Ala Ala Asn Ala
305                 310                 315                 320

Val Ile Gly Thr Asp Asn Gly Ala Gly Arg
                325                 330


<210> SEQ ID NO 11
<211> LENGTH: 5258
<212> TYPE: DNA
<213> ORGANISM: Rickettsia typhi

<400> SEQUENCE: 11

cgacaattag cccgtagttt agaaactatt aaaacaaaat atttaggtta tttccttatc      60

aaatgtggga tatcttgact catatttgat taatttgttt taatactaga tactaaattt     120

taacttaaat atgggaaaaa attatggctc aaaaaccaaa ttttctaaaa aaaataattt     180

ccgcaggatt ggtaactgct tccacggcta ctatagttgc tggtttttct ggtgtagcaa     240

tgggtgctgt tatgcaatat aatagaacaa caaatgcagc agctacaact gttgatggtg     300

caggatttga tcaaactggc gctggtgtta atcttcctgt cgctacaaat tcggttatta     360

ctgctaattc taataatgct attactttta atactccaaa cggtaattta aatagtttgt     420

ttttggatac tgcaaatact ttagcagtaa caattaatga aaatactacc ttagggtttg     480

taactaatgt tactaaacag ggtaacttct ttaattttac tattggtgct ggtaaaagtc     540

ttaccataac aggtcatggt attactgctc aacaagctgc tactacaaaa agtgctcaaa     600

atgttgtttc aaaagttaat gctggtgctg ctattaacga taatgatctt agcggtgtag     660

gatcaataga ctttactgct gcgccttctg tattagaatt taatttaata aatcctacaa     720

ctcaagaagc tcctcttaca cttggtgata atgctaaaat agttaatggt gctaatggga     780

tattaaatat tactaatggg tttgttaagg tttcagataa aacttttgct ggtattaaga     840

caattaatat cggtgataat caaggtttaa tgtttaatac tactcctgat gccgctaatg     900
```

-continued

```
ctttaaattt gcaaggaggt ggtaatacta ttaattttaa tggaagagac ggtactggta    960
aattagtatt ggtcagtaag aatggcaatg ctactgaatt taatgttaca ggaagtttag   1020
gcggtaatct aaaaggtgtt attgaatttg atactacagc agcagctggt aagcttatcg   1080
ctaatggagg tgctgctaat gcagtaatag gtacagataa tggagcaggt agagctgcag   1140
gatttattgt tagtgttgat aatggtaatg cagcaacaat ttccggacag gtttatgcta   1200
aagacatagt tatacaaagt gctaatgcag gtggacaagt cacttttgaa catttagttg   1260
atgttggttt aggcggtaag accaatttta aaaccgcaga ttctaaagtt ataataacag   1320
aaaacgcaag ctttggttct actgattttg gtaatcttgc agtacagatt gtagtgccta   1380
ataataagat acttacaggt aatttcatag gtgatgcaaa aaataacggt aatactgcag   1440
gtgtgatcac ttttaatgct aatggtactt tagtaagtgg taatactgat ccaaatattg   1500
tagtaacaaa tattaaggca atcgaagtag aaggtgccgg gattgtacaa ttatcaggaa   1560
tacatggtgc agaattacgt ttaggaaatg ctggctctat ctttaaactt gctgatggca   1620
cagtgattaa cggtccagtt aaccaaaatc ctcttgtgaa taataatgcg cttgcagctg   1680
gttctattca gttagatgga agtgctataa ttaccggtga tataggtaac ggtgctgtta   1740
atgctgcgtt acaagacatt actttagcta atgatgcttc aaaaatatta acacttagtg   1800
gggcaaatat tatcggcgct aatgctggtg gtgcaattca ttttcaagct aacggtggta   1860
ctattcaatt aacaagcact caaaataata ttttagttga ttttgattta gatgtaacta   1920
ctgatcaaac aggtgttgtt gatgcaagta gtttaacaaa taatcaaact ttaactatta   1980
atggtagcat cggtactatt ggcgctaata ctaaaacact tggaagattt aatgttgggt   2040
caagtaaaac aatattaaat gctggagatg ttgctattaa cgagttagtt atggaaaatg   2100
atggttcagt acaccttact cacaatactt acttaataac aaaaactatc aatgctgcaa   2160
atcaaggtaa aatcatagtt gccgctgatc ctattaatac tgatacagct cttgctgatg   2220
gtacgaattt aggtagtgca gaaagtccac tttctaatat tcattttgct actaaagctg   2280
ctaatggtga ctctatatta catataggta aaggagtaaa tttatatgct aataatatta   2340
ctactaccga tgctaatgta ggttctttac actttaggtc tggtggaacc agtatagtaa   2400
gtggtacagt tggtggacag caaggtctta agcttaataa tttaatatta gataatggta   2460
ctactgttaa gtttttaggt gatatcacat ttaatggtgg tactaaaatt gaaggtaaat   2520
ctatcttgca aattagcagc aattatatta ctgatcatat tgaatctgct gataatactg   2580
gtacattaga atttgttaat actgatccta tcaccgtaac gttaaataaa caaggtgctt   2640
attttggtgt tttaaaacaa gtaatggttt ctggtccagg taacatagca tttaatgaga   2700
taggtaatgg agttgcacat gctatagcag ttgattccat ttcttttgaa aatgcaagtt   2760
taggtgcatc tttattctta cttagtggca ctccattaga tgtgctaaca attaaaagta   2820
ccgtaggtaa tggtacagta gataatttta atgctcctat tttagttgta tcaggtattg   2880
atagtatgat caataacggt caagttatcg gtgatcaaaa gaatattata gctctatcgc   2940
ttggaagtga taacagtatt actgttaatt ctaatacatt atatgcaggt atcagaacta   3000
ctaaaactaa tcaaggtact gttacactta gcggtggtat acctaataac cctggtacaa   3060
tttatggttt aggtttagag aatggtgatc caaagttaaa gcaagtaacg tttactacag   3120
attataacaa cttaggtagt attattgcaa ctaacgtaac aattaatgac gatgtaacac   3180
ttactacagg aggtatagcc gggacagatt ttgacggtaa aattactctt ggaagtatta   3240
acggtaatgc taatgtaaag tttgttgaca gaacattttc tcatcctaca agtatgattg   3300
```

```
tttctactaa agctaatcag ggtactgtaa cttatttagg taatgcatta gtcggtaata   3360
ttggtagttc agatattcct gtagcttctg ttagatttac tggtaatgat agtggtgtag   3420
gattacaagg caatattcac tcacaaaata tagactttgg tacttataac ttaactattt   3480
taaattctga tgtaatttta ggcggtggta ctactgctat taatggtgag attgatcttt   3540
tgacaaataa tttaatattt gcaaatggta cttcaacatg gggcaataat acctctctta   3600
gtacaacatt aaacgtatca aacggtaatg taggtcaaat agttattgct gaaggtgctc   3660
aagttaatgc aacaactaca ggaactacaa ccattaaaat acaagataat gctaatgcaa   3720
atttcagtgg tacacaaact tatactttaa tccaaggtgg tgccagattt aacggtactt   3780
taggagctcc taactttgat gtaacaggaa ataatatttt cgtaaaatat gaattaatac   3840
gtgatgcgaa tcaggattat gtgttaacac gtactaacga tgtattaaat gtagttacaa   3900
cagctgtagg aaatagtgca attgcaaatg cacctggtgt acatcaaaat attgctatat   3960
gcttagaatc aactgataca gcagcttata ataatatgct tttagctaaa gattcttctg   4020
atgtcgcaac atttatagga gctattgcta cagatacagg tgctgctgta gctacagtaa   4080
acttaaatga tacacaaaaa actcaagatc tacttggtaa taggctaggt gcacttagat   4140
atctaagtaa ttctgaaact gctgatgttg gtggatctga aacaggtgca gtatcttcag   4200
gtgatgaagc gattgatcaa gtatcttatg gtgtatgggc taaacctttc tataacatcg   4260
cagaacaaga taaaaaaggt ggtctagctg gttataaagc aaaaactgct ggtgttgtag   4320
ttggtttaga tactctcgct aatgataacc taatgattgg tgcagctatt ggtatcacta   4380
aaactgacat aaaacaccaa gattataaaa aaggtgataa aactgatatt aagggtttat   4440
ccttctctct atatggtgcc cagcagcttg ttaagaattt ctttgctcaa ggtagtgcaa   4500
tatttacctt aaacaaagtc aaaagtaaaa gtcagcgtta cttcttcgat gctaatggta   4560
agatgaacaa gcaaattgct gccggtaatt atgataacat aacattcggt ggtaatttaa   4620
tgtttggtta tgattataat gcactgcaag gtgtattagt gactccaatg gcagggctta   4680
gctacttaaa atcttctaat gaaaactata aagaaactgg tactacagtt gcaaataagc   4740
gcattcacag caaatttagt gatagaatcg atttaatagt aggtgctaaa gtaactggta   4800
gtgctatgaa tataaatgat attgtgatat atccagaaat tcattctttt gtagtgcaca   4860
aagtaaatgg taagctatct aaggctcagt ctatgttaga tggacaaact gctccattta   4920
tcagtcagcc tgatagaact gctaaaacat cttataatat aggcttaagt gcaaatataa   4980
gatctgatgc taagatggag tatggtatcg gttatgattt taatgctgca agtaaatata   5040
ctgcacatca aggtacttta aaagtacgta taaatttcta atcattattg atgagtttag   5100
tgagtttata acttgatcaa gaaaaaagcc catttttttt aaactgggct tttttctatt   5160
tacttatgta atgaggtctt actgtatacg tagtattgca atcattgata ctaaagtctc   5220
tttcattgtc aaagtaatat tcgcaatcta gagaataa                          5258
```

```
<210> SEQ ID NO 12
<211> LENGTH: 2130
<212> TYPE: DNA
<213> ORGANISM: Rickettsia typhi

<400> SEQUENCE: 12

atgggtgctg ttatgcaata taatagaaca acaaatgcag cagctacaac tgttgatggt     60
gcaggatttg atcaaactgg cgctggtgtt aatcttcctg tcgctacaaa ttcggttatt    120
actgctaatt ctaataatgc tattactttt aatactccaa acggtaattt aaatagtttg    180
```

-continued

```
tttttggata ctgcaaatac tttagcagta acaattaatg aaaatactac cttagggttt    240
gtaactaatg ttactaaaca gggtaacttc tttaatttta ctattggtgc tggtaaaagt    300
cttaccataa caggtcatgg tattactgct caacaagctg ctactacaaa aagtgctcaa    360
aatgttgttt caaaagttaa tgctggtgct gctattaacg ataatgatct tagcggtgta    420
ggatcaatag actttactgc tgcgccttct gtattagaat ttaatttaat aaatcctaca    480
actcaagaag ctcctcttac acttggtgat aatgctaaaa tagttaatgg tgctaatggg    540
atattaaata ttactaatgg gtttgttaag gtttcagata aaacttttgc tggtattaag    600
acaattaata tcggtgataa tcaaggttta atgtttaata ctactcctga tgccgctaat    660
gctttaaatt tgcaaggagg tggtaatact attaatttta atggaagaga cggtactggt    720
aaattagtat tggtcagtaa gaatggcaat gctactgaat ttaatgttac aggaagttta    780
ggcggtaatc taaaaggtgt tattgaattt gatactacag cagcagctgg taagcttatc    840
gctaatggag gtgctgctaa tgcagtaata ggtacagata atggagcagg tagagctgca    900
ggatttattg ttagtgttga taatggtaat gcagcaacaa tttccggaca ggtttatgct    960
aaagacatag ttatacaaag tgctaatgca ggtggacaag tcacttttga acatttagtt   1020
gatgttggtt taggcggtaa gaccaatttt aaaaccgcag attctaaagt tataataaca   1080
gaaaacgcaa gctttggttc tactgatttt ggtaatcttg cagtacagat tgtagtgcct   1140
aataataaga tacttacagg taatttcata ggtgatgcaa aaaataacgg taatactgca   1200
ggtgtgatca cttttaatgc taatggtact ttagtaagtg gtaatactga tccaaatatt   1260
gtagtaacaa atattaaggc aatcgaagta gaaggtgccg ggattgtaca attatcagga   1320
atacatggtg cagaattacg tttaggaaat gctggctcta tctttaaact tgctgatggc   1380
acagtgatta acggtccagt taaccaaaat cctcttgtga ataataatgc gcttgcagct   1440
ggttctattc agttagatgg aagtgctata attaccggtg atataggtaa cggtgctgtt   1500
aatgctgcgt tacaagacat tactttagct aatgatgctt caaaaaatatt aacacttagt   1560
ggggcaaata ttatcggcgc taatgctggt ggtgcaattc attttcaagc taacggtggt   1620
actattcaat taacaagcac tcaaaataat attttagttg attttgattt agatgtaact   1680
actgatcaaa caggtgttgt tgatgcaagt agtttaacaa ataatcaaac tttaactatt   1740
aatggtagca tcggtactat tggcgctaat actaaaacac ttggaagatt taatgttggg   1800
tcaagtaaaa caatattaaa tgctggagat gttgctatta acgagttagt tatggaaaat   1860
gatggttcag tacaccttac tcacaatact tacttaataa caaaaactat caatgctgca   1920
aatcaaggta aaatcatagt tgccgctgat cctattaata ctgatacagc tcttgctgat   1980
ggtacgaatt taggtagtgc agaaagtcca ctttctaata ttcattttgc tactaaagct   2040
gctaatggtg actctatatt acatataggt aaaggagtaa atttatatgc taataatatt   2100
actactaccg atgctaatgt aggttcttaa                                    2130
```

RECOMBINANT ANTIGENS FOR DIAGNOSIS AND PREVENTION OF MURINE TYPHUS

CROSS-REFERENCE TO RELATED APPLICATIONS

This application is a divisional application of application Ser. No. 11/789,122 filed Apr. 18, 2007 now U.S. Pat. No. 7,544,778 and claims priority to U.S. Provisional application 60/793,583 filed Apr. 20, 2006.

SEQUENCE LISTING

I hereby state that the information recorded in computer readable form is identical to the written sequence listing.

BACKGROUND OF THE INVENTION

1. Field of the Invention

This invention relates to a gene and protein which can be used for vaccination against and/or for the detection and identification of *R. typhi*. More particularly, the invention relates to a specific nucleotide sequence encoding a highly specific and immunogenic portion of the gene encoding the protective S-layer protein antigen of *Rickettsia prowazekii* and the polypeptide products of this gene. The polypeptide sequence can be utilized in diagnostic and detection assays for murine typhus and as an immunogen useful as a component in vaccine formulations against murine typhus.

2. Description of the Prior Art

Murine (endemic or flea-borne) typhus, caused by infection with *Rickettsia typhi*, is a zoonosis that involves rats (*Rattus rattus* and *R. norvegicus*) as the main reservoir and the oriental rat flea (*Xenopsylla cheopis*) as the main vector [1,2]. The infection is primarily caused by scratching the flea bitted site and self-inoculating the *R. typhi*-laden feces, or directly by infected flea bite [3]. The symptoms of murine typhus include fever, headache, enlarged local lymph nodes and rashes on the trunk. These clinical manifestations are non-specific and resemble many other diseases such as viral infections, typhoid fever, leptospirosis, epidemic typhus and scrub typhus [3,10]. As a result, murine typhus is frequently misdiagnosed and its incidence is probably grossly underestimated.

Murine typhus is one of the most widely distributed arthropod-borne diseases of humans and occurs in a variety of environments from hot and humid lowlands to semi-arid highlands including Australia [6], Spain [7], Indonesia [8], and southwestern United States [9] in addition to previously reported countries including China, Thailand, Kuwait, Israel, and Vietnam [3,5]. It is often found in international port cities and costal regions where rodents are common [3-5].

The diagnosis of murine typhus relies mainly on serological methods [11]. The old serological assay, Weil-Felix test, is based on the detection of antibodies to *Proteus vulgaris* OX-19 that contains cross reactive epitopes of *Rickettsia [*12, 13]. However, determination of *R. typhi* infection by the Weil-Felix test requires a qualitative determination and therefore somewhat subjective. Additionally, because the Weil-Felix reaction requires specialized reagents, many facilities especially in rural areas or in developing countries often may not be capable of performing the laboratory diagnosis.

Other techniques include immuno-fluorescence assay (IFA) and complement fixation (CT) tests were adapted for the detection of antibodies specific for rickettsiae [14-16]. Current serodiagnostic assays such as the ELISA, Dip-S-Ticks (DS), indirect immunofluorescent antibody (IFA) and indirect peroxidase assays [17,18] require the propagation of rickettsiae in infected yolk sacs of embryonated chicken eggs or cell cultures to prepare the antigens used in these assays. However, only a few specialized laboratories have the ability to culture and purify rickettsiae, which requires Biosafety level three (BSL-3) containment facilities. Additionally, because the organism is required for the assay, in addition to potential biosafety hazards associated with the assay, these assay methods also suffer from refrigerated storage requirements, and the problem of reproducibility associated with frequent production of rickettsial antigens.

In addition to antibody-based assays, polymerase chain reaction (PCR) amplification of rickettsial protein antigen genes has been demonstrated as a reliable diagnostic method, and genotypes can be determined without isolation of the organism [19,20]. However, gene amplification requires sophisticated instrumentation and reagents generally not available in most medical facilities especially those far forward. Based on these considerations, production of recombinant antigens of *R. typhi* is a logic direction for the development of serological assays and vaccine candidates for murine typhus.

*R. typhi* has a monomolecular layer of protein arranged in a periodic tetragonal array on its surface [21]. This crystalline layer, representing 10 to 15% of the total protein mass of the *rickettsia*, was identified as the immunodominant species-specific surface protein antigen OmpB. It has been isolated, purified, and biochemically characterized [22-25]. The earliest and dominant immunological responses in mice, guinea pigs, rabbits, and humans, following infection with *R. typhi*, are directed against Omp B [17, 4, 25]. We have shown that purified native typhus OmpB induces strong humoral and cell mediated immune responses. Protective immunity was elicited by typhus OmpB in guinea pig and mouse protection models [26-29].

Based on these observations, therefore, OmpB is a particularly advantageous target for developing diagnostic reagents. *R. prowazekii*, the etiologic agent of epidemic typhus, also belongs to the typhus group of rickettsiae and its OmpB exhibits similar antigenic and chemical structures to those of *R. typhi*. Therefore, cross-reactivity of antibody to OmpB between these two species is inevitable. Cross absorption of test serum is needed to distinguish between them these to species [10].

The whole ORF of OmpB codes for a polypeptide of 1642 amino acids. The native matured protein does not contain the leader peptide at the N-terminus and the β-sheet peptide at the C-terminus. The expression of the intact OmpB protein (135 kDa) has been attempted. However, the full-length product was shown to be toxic to *Escherichia coli* and rapidly degraded. Moreover, due to its large size and high content of β-sheet structure, refolding of the full-length gene product was not successful.

SUMMARY OF THE INVENTION

Accordingly, an object of this invention are methylated and unmethylated recombinant polypeptides encompassing immunologically active regions of OmpB of *Rickettsia typhi*.

Another object of the invention is a method of using the methylated or unmethylated recombinant OmpB fragments in antibody-based assays for the detection of exposure to *Rickettsia typhi*.

A still further object of the invention is the use of OmpB or the OmpB fragments as an immunogen.

DESCRIPTION OF THE PREFERRED EMBODIMENTS

Evaluation of *Rickettsia typhi* proteins has led to the identification of OmpB is an exceptionally promising candidate as a reagent for use in diagnostic and detection assays as well as components in vaccine formulations. The species-specific surface protein antigen OmpB of *R. typhi* was identified as the immunodominant. The earliest and dominant immunological anti-protein responses of mice, guinea pigs, rabbits, and humans following infection with *R. typhi* are directed against this Omp B antigen. These observations suggested OmpB as an appropriate target for developing diagnostic reagents.

Figure 1:
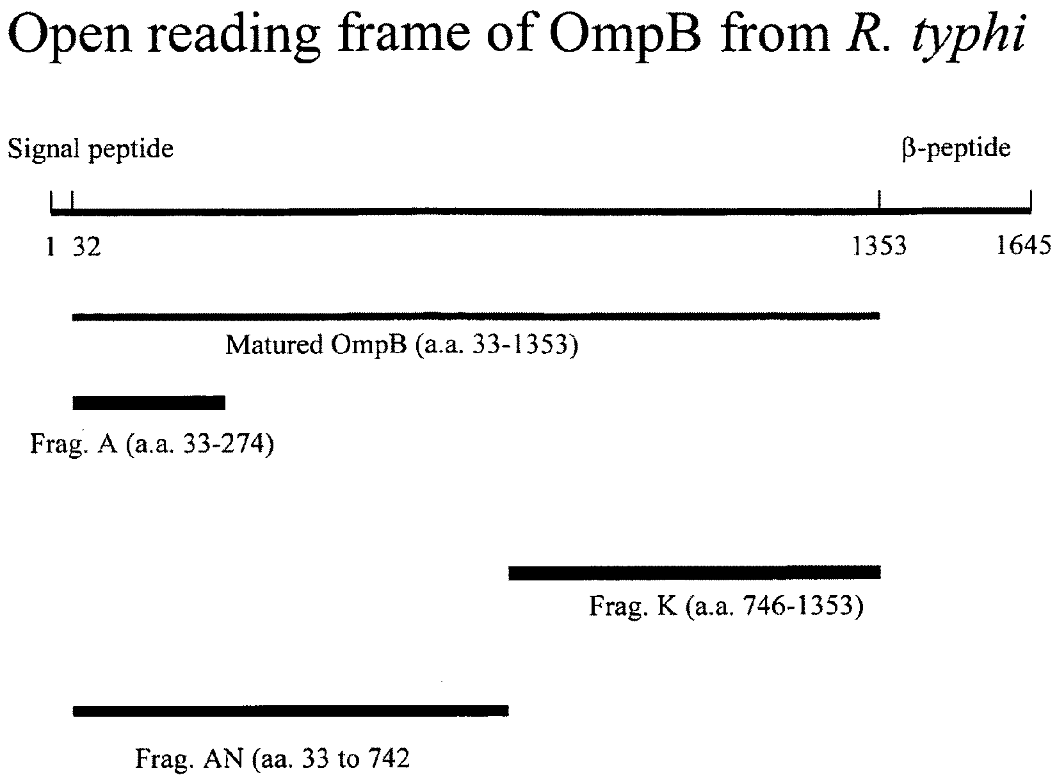
FIG. 1. Open reading frame of OmpB and location of Fragments A, K and AN.

Central to the development of improved detection and diagnostic immunoassay methods and standardization is the development of more effective antigens for use in existing antibody-based methods. In order to improve the antigenicity and potential immunogencity of the OmpB, specific regions of OmpB were evaluated for sera reactivity. Western blot analysis of partially digested OmpB revealed that all the reactive fragments were larger than 20 kDa [31]. One reactive fragment was located at the N-terminus and another located at the C-terminus. Along these lines, efforts have been made to identify immunodominant fragments of OmpB proteins. Accordingly, two highly sera-reactive protein fragments (Fragment A and Fragment K) have been identified. FIG. 1 illustrates the location of these fragments within the OmpB molecule. The amino acid sequence of OmpB is illustrated in SEQ ID No. 10, which is encoded by nucleotide the sequence of SEQ ID No. 11. Also identified is Fragment AN, which encompasses Fragment A. The location Fragment AN, which has the amino acid sequence of SEQ ID No. 9 and is encoded by nucleotide sequence SEQ ID No. 12, is also illustrated in FIG. 1.

Fragment A and Fragment K of OmpB from *R. typhi* were successfully cloned, expressed, purified, and refolded. Both fragments have been shown to be recognized by different patient sera and can be used to replace whole cell antigens and/or native OmpB as a diagnostic marker and a potential vaccine candidate. The reactivity of Fragment A has been increased by methylation. The reactivity of Fragment K with patient sera was not as good as that of native OmpB, it is possibly due to the fact that Kt covers only ½ of the whole OmpB. The improvement may be made by methylation of the fragment K and/or combining A and K to provide more reactive epitopes.

Construction of recombinant *R. typhi* protein A Fragment was carried out by first producing a cDNA copy of the gene sequence by polymerase chain reaction. A primer pair was designed using the nucleotide sequence of the ORF of *R. typhi* OmpB. The forward primer (SEQ ID No. 5) contained the methionine initiation codon, at residue 33, which is part of the Nde I recognition sequence. The reverse primer (SEQ ID No. 6) mutated the lysine codon at residue 273 to a stop codon and contained a Barn HI site. Fragment A has the amino acid sequence of SEQ ID No. 2 and is encoded by the nucleotide sequence of SEQ ID No. 1.

The coding sequence from amino acid 33 to 272 was amplified by PCR from DNA isolated *R. typhi* Wilminton strain. The fragment A gene was amplified in a mixture of 400 mM each of deoxynucleotide triphosphate, 1 μM of each primer, 1.5 U of Taq polymerase (Perkin Elmer-Cetus, Norwalk Conn.) in 10 mM Tris-HCl buffer, pH 8.3, 1.5 mM $MgCl_2$, and 50 mM KCl. The PCR reaction was started with 5 min at 94 C, and followed by 30 cycle of 94 C for 50 second, 55 C for 1 mM and 72 C for 2 min. the last cycle was extended for 10 min at 72 C. the amplified gene fragment was digested with Nde I (New England BioLabs, Beverly, Mass.) and BamH I (GIBCO-BRL Life Technology, Gaithersburg, Md.) and ligated with doubly digested expression vector pET11a.

Fragment A was expressed as inclusion body in *E. coli* BL21. The inclusion bodies were extracted with 2 M urea twice followed by 2% deoxycholate twice. The final pellet was dissolved in 8 M urea and refolded by sequential dialysis in decreasing concentrations of urea. The chemical methylation of fragment A was performed according to the procedures described by Taralp and Kaplan (J. Prot. Chem. 16, 183-193, 1997).

For construction of fragment K, a primer pair was designed using the nucleotide sequence of the ORF of *R. typhi* OmpB. The forward primer (SEQ ID No. 7) contained the arginine residue 745 codon AGG and changed to ATG as the initiation codon for methionine, which is part of the Nde I recognition sequence. The reverse primer (SEQ ID No. 8) mutated the serine 1354 TCA to a stop codon TAA and contained a Bam HI site. Fragment K has amino acid sequence of SEQ ID No. 4 and is encoded by the DNA sequences of SEQ ID No. 3.

The coding sequence from amino acid 745 to 1353 was amplified by PCR from DNA isolated *R. typhi* Wilminton strain. The fragment K gene was amplified in a 50 ul mixture of 150 mM each of deoxynucleotide triphosephate, 0.8 μM of each primer, 2.5 U of Taq Gold polymerase (Perkin Elmer-Cetus, Norwalk Conn.) in 10 mM Tris-HCl buffer, pH 8.3, 1.5 mM $MgCl_2$, and 50 mM KCl. The PCR reaction was started with 10 min at 94 C, and followed by 30 cycle of 94 C for 30 second, 55 C for 30 second and 72 C for 2 min. the last cycle was extended for 7 min at 72 C. The ligation of the amplified fragment K in to pET11a was the same as for fragment A.

Fragment K was over-expressed in BL21 cells by induction with 1 mM IPTG for 4 hr. The over-expressed K was primarily in the inclusion body and was extracted with 4 M urea. The solubilized K in 4 M urea was further purified with HPLC using two gel filtration columns in tandem (TSK-G3000-SW and TSK-G4000-SW) followed by an anion exchange column using a NaCl gradient (50-100 mM in 30 minutes). A greater than 95% purity as demonstrated by SDS-PAGE. The purified K was refolded by dialysis in 2 M urea at 4° C. with two changes of dialysis solution in the presence of reduced glutathione (1 mM), followed by dialysis in buffer without urea.

Expression of Fragment A and K was accomplished by inserting the encoding DNA into a suitable expression system, such as pET 24a. The *R. typhi* recombinant protein antigen can be utilized as an antigen either as an unpurified *E. coli* lysate or purified by any number of methods and subsequently used as antigen in detection or diagnostic assays.

In order to ascertain if antigenicity of the fragments could be positively affected by methylation, Fragment A, located at the N-terminus (aa 33-273) was expressed in *E. coli*, purified, refolded, and then chemically methylated in vacuum using CH3I. The sites of multiple methylation, mon-, di-, tri-methylation were characterized by liquid chromatography/Mass Spectroscopy (LC/MS) [32].

Figure 2:
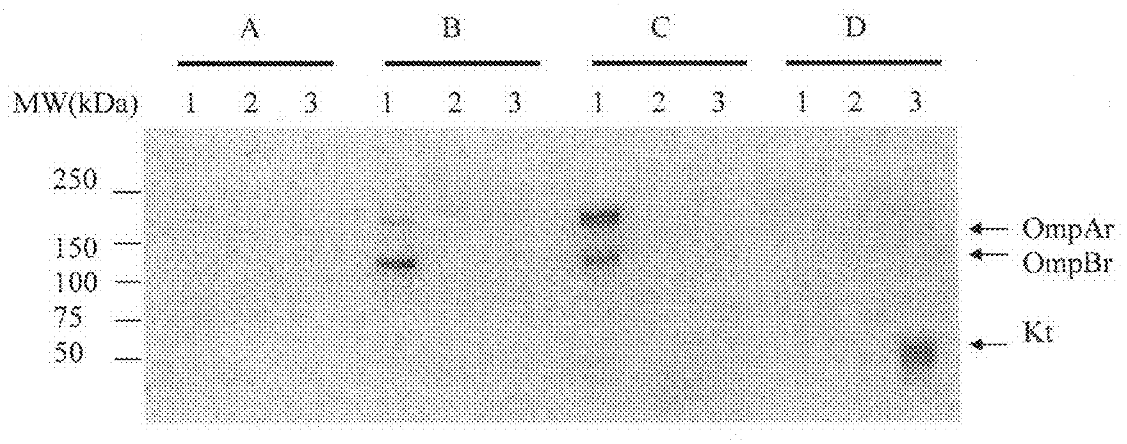
FIG. 2. Western blot analysis of native and recombinant antigens.

FIG. 2 illustrates the specificity of the recombinant Fragment K by western blot analysis. In FIG. 2, no reactivity was observed against OmpA or OmpB using control sera. However, both OmpA and B from *Rickettsia rickettsii* are clearly identifiable using anti-*R. rickettsii* sera (Panel B). The lack of response in lane two of Panel B likely indicates that folding in the OmpAB chimera abrogates normally available epitopes. These same proteins were observed when anti-*R. prowazekii* sera was used, illustrating the presence of cross-reactive epitopes between *R. rickettsii* and *R. prowazekii*. However, anti-*R. typhi* sera only bound to Fragment K but not OmpA or OmpB from *R. rickettsii* (Panel D).

These studies demonstrated a significant increase in sero-reactivity of fragment A (i.e., Fragment A from *R. typhi*) subsequent to chemical methylation, compared to unmethylated Fragment A. The reader is referred to Table 1, showing enzyme-linked immunosorbent assay (ELISA) results of 48 *R. typhi* immune sera on Fragment A, before and after methylation. As shown in Table 1, a robust anti-Fragment A reactivity is evident, especially for IgG, in comparison to sera responses against LPS as antigen. Recent evaluation of this methylated fragment A has shown that more than 50% of 37 confirmed positive sera with whole cell antigen were reactive, indicating that although fragment A contains important diagnostic epitopes. The results also indicate that other important epitopes are located within OmpB but not contained in Fragment A. These initial results strongly suggest that recombinant protein fragments encompass the other parts of OmpB is necessary and methylation of the recombinant proteins, either chemically or enzymatically, can increase the sensitivity of the serodiagnosis.

TABLE 1

| ELISA titers from fragment A of *R. typhi* | | | | | | |
|---|---|---|---|---|---|---|
| | IgG | | | IgM | | |
| Patient sera | *R. typhi* LPS | Before Methylation | After methylation | *R. typhi* LPS | Before methylation | After methylation |
| 1 | 800 | 800 | 400 | 12800 | 1600 | 400 |
| 2 | 800 | 800 | 800 | 0 | 100 | 100 |
| 3 | 0 | 100 | 0 | 0 | 800 | 800 |
| 4 | 100 | 800 | 800 | 0 | 800 | 800 |
| 5 | 0 | 800 | 0 | 12800 | 100 | 400 |
| 6 | 100 | 800 | 1600 | 100 | 200 | 12800 |
| 7 | 0 | 100 | 0 | 12800 | 400 | 1600 |
| 8 | 1600 | 800 | 800 | 12800 | 400 | 1600 |
| 9 | 0 | 100 | 0 | 12800 | 1600 | 6400 |
| 10 | 0 | 200 | 0 | 100 | 400 | 800 |
| 11 | 100 | 100 | 100 | 6400 | 400 | 400 |
| 12 | nt | 0 | 100 | 12800 | 400 | 400 |
| 13 | nt | 0 | 100 | 12800 | 200 | 800 |
| 14 | 3200 | 6400 | 3200 | 100 | 100 | 100 |
| 15 | 1600 | 6400 | 1600 | 0 | 200 | 200 |
| 16 | 0 | 200 | 0 | 0 | 100 | 400 |
| 17 | 0 | 100 | 0 | 0 | 100 | 400 |
| 18 | Nt | 200 | 0 | Nt | 100 | 200 |
| 19 | 100 | 200 | 12800 | 1600 | 6400 | 51200 |
| 20 | 400 | 1600 | 800 | 800 | 800 | 100 |
| 21 | 800 | 1600 | 1600 | 12800 | 800 | 100 |
| 22 | 0 | 800 | 0 | 0 | 100 | 100 |
| 23 | 0 | 400 | 0 | 0 | 0 | 0 |
| 24 | 0 | 200 | 100 | 200 | 1600 | 3200 |
| 25 | 0 | 200 | 100 | 3200 | 1600 | 1600 |
| 26 | 200 | 3200 | 6400 | 0 | 6400 | 6400 |
| 27 | 100 | 1600 | 1600 | 0 | 800 | 800 |
| 28 | 0 | 200 | 100 | 0 | 800 | 400 |
| 29 | 0 | 200 | 200 | 0 | 800 | 400 |
| 30 | 0 | 1600 | 0 | 1600 | 200 | 100 |
| 31 | 200 | 3200 | 51200 | 12800 | 200 | 800 |
| 32 | 400 | 6400 | 6400 | 0 | 100 | 1600 |
| 33 | 400 | 6400 | 6400 | 0 | 0 | 1600 |
| 34 | 100 | 400 | 400 | 0 | 0 | 0 |
| 35 | 800 | 200 | 800 | 0 | 0 | 0 |
| 36 | 1600 | 800 | 1600 | 12800 | 800 | 6400 |
| 37 | 0 | 400 | 3200 | 12800 | 800 | 25600 |
| 37 | 400 | 400 | 400 | 0 | 100 | 100 |
| 39 | 800 | 1600 | 800 | 400 | 100 | 100 |
| 40 | 800 | 800 | 800 | 0 | 100 | 800 |
| 41 | 800 | 1600 | 3200 | 0 | 200 | 1600 |
| 42 | 12800 | 1600 | 1600 | 12800 | 100 | 100 |
| 43 | 12800 | 1600 | 1600 | 12800 | 0 | 100 |
| 44 | 0 | 1600 | 0 | 12800 | 800 | 1600 |
| 45 | 200 | 6400 | 6400 | 12800 | 800 | 1600 |
| 46 | 400 | 3200 | 6400 | 400 | 400 | 1600 |
| 47 | 200 | 3200 | 3200 | 200 | 800 | 1600 |
| 48 | 800 | 800 | 3200 | 800 | 800 | 3200 |
| 49 | 800 | 3200 | 12800 | 800 | 1600 | 51200 |
| 50 | 400 | 1600 | 6400 | 400 | 800 | 12800 |
| 51 | NT | 400 | 800 | NT | 800 | 400 |

Based on these results, these protein fragments will be valuable antigens in detection and diagnostic assays. Standardization of antigen will improve assay diagnostic performance and provide early and more accurate treatment regimens. Improved sensitivity can be achieved by combination of protein fragments containing a greater number of epitopes well represented in serum antibody repertoires.

Accordingly, an aspect of this invention is the recombinant expression of immunodominant fragments of an outer membrane protein OmpB. Another aspect of this invention is the methylation of recombinant protein fragments to mimic the rickettsial derived OmpB for increased seroreactivity. Therefore, these protein fragments, recombinantly produced and either used alone or in combination will confer improved standardization and concomitant assay reproducibility and potentially sensitivity in assays for the detection and diagnostic assays for *R. typhi* infection and murine typhus.

The following examples are provided to further illustrate the use of the invention.

EXAMPLE 1

Use of OmpB Fragments A and K as Diagnostic Reagent

Assays using the recombinantly produced proteins include antibody-based assays such as enzyme-linked immunosorbent assays. As previously mentioned, antigen for the assay can be in the form of unpurified *E. coli* lysate. However, for increased assay sensitivity and reduced background, purified recombinant *R. typhi* proteins can be used and in methylated form. As an illustration, the following procedure is provided, comprising the following steps:

1. Recombinant proteins represented by SEQ ID No. 2, 4, 9 or 10 are immobilized, such as in 96-well plates. Alternatively, for increased sensitivity and specificity of the assay, both of the recombinant proteins represented by SEQ ID No. 2, 4, 9 or 10 can be included together or immobilized separately but used in the same assay;
2. Wash off unreacted/unbound antigen. A preferred embodiment of the inventive method is to wash at least 3 times with wash buffer containing 0.1% polysorbate surfactant such as polyoxyethylene (20) sorbitan monolaurate;
3. Block unreacted sites. In a preferred embodiment, blocking of unreacted sites is accomplished with 5% skim milk in wash buffer)×45 minutes and then rinsed three times.
4. React test sera to the bound antigen;
5. Plates are washed three times with wash buffer;
6. After incubating the test sera, the bound antibody-antigen is exposed to a probe. In a preferred embodiment, the probe is enzyme-labeled (e.g. peroxidase) anti-human immunoglobulin;
7. detecting bound probe. Detection of bound probe can by any number of methods. In a preferred embodiment, detection is by measurement of enzymatic reaction of added substrate.

The above specific procedural outline is provided to illustrate the general method of using the fragments for the detection *R. typhi* infection. However, other iterations of the general antibody-based procedure is contemplated. Furthermore, a standard curve can be constructed by conducting the above ELISA procedures with the recombinant proteins but utilizing a range of concentrations of specific antibody to *R. typhi*. The extent of measured binding of patient serum antibody is compared to a graphic representation of the binding of the *R. typhi*-specific antibody concentrations.

EXAMPLE 2

Prophetic Use of Recombinant *R. typhi* Proteins as a Vaccine Component

The recombinantly produced polypeptides, because of their immunoreactivity to antibody in patient sera are excellent vaccine candidates. Accordingly, all or a fragment of the *R. typhi* proteins: Fragment A, Fragment K or Fragment AN (SEQ ID No. 2, 4, or 9 respectively), or their respective DNA sequences (SEQ ID No. 1, 3 and 12) incorporated into a suitable expression vector system, can be utilized as vaccine components. The method for induction of *R. typhi* immunity contains the following steps:

a. administering an immunogenic composition containing the entire or immunogenic fragments of the recombinant polypeptides selected from the group consisting of SEQ ID No. 2, 4 or 9 in a unit dose range of 50 μg to 2 mg;
b. administration of boosting dose of said immunogenic composition at least 1 week after priming dose with unit dose range of 50 μg to 2 mg in a buffered aqueous solution, wherein an immune response is elicited.

An alternative method of immunizing is to administer DNA sequences encoding Fragments A, K or AN, or combinations thereof, inserted into a suitable expression system capable of expressing the fragments in vivo. Suitable expression systems can include viral expression vectors as well as a number of available DNA vector systems.

REFERENCES

1. Ito, S., J. W. Vinson & T. J. McGuire, Jr. 1975. Murine typhus Rickettsiae in the oriental rat flea. Ann. N.Y. Acad. Sci. 266: 35-60
2. Farhang-Azad, A., R. Traub & C. L. Wisseman, Jr. 1983. *Rickettsia mooseri* infection in the fleas *Leptopsylla segnis* and *Xenopsylla cheopis*. Am. J. Trop. Med. Hyg. 32: 1392-1400
3. Azad A F. Epidemiology of murine typhus. Annu Rev Entomol 1990; 35:553-69.
4. Kelly D J, Richards A L, Temenak J J, Strickman D, Dasch G A. The past and present threat of rickettsial diseases to military medicine and international public health. Clin Infect Dis 2002; 34(suppl 4):s145-s169.
5. Traub, R., C. L. Wisseman & A. Farhang-Azad. 1978. The ecology of murine typhus-a critical review. Trop. Dis. Bull. 75: 237-317
6. Jones, S L, Athan E, O'Brien D, Graves S R, Ngyuyen C, Stenos J. Murine typhus: the first reported case from Victoria. Med. J. Aust. 2004 May 3; 180(9):482.
7. Lledo L, Gegundez I, Ruiz E, Rodriguez L, Bacellar F, Saz J V. *Rickettsia typhi* infection in wild rodents from central Spain. Ann Trop Med. Parasitol. 2003 June; 97(4):411-4.
8. Richards A L, Rahardjo E, Rusjdi A F, Kelly D J, Dasch G A, Church C J, Bangs M J. Evidence of *Rickettsia typhi* and the potential for murine typhus in Jayapura, Irian Jaya, Indonesia. Am J Trop Med. Hyg. 2002 April; 66(4):431-4.
9. Walker, D. H., F. M. Parks, T. G. Betz, et al. 1989. Histopathology and immunohistologic demonstration of the distribution of *Rickettsia typhi* in fatal murine typhus. Am. J. Clin. Pathol. 91: 720-724
10. La Scola B, Rydkina L, Ndihokubwayo J B, Vene S, Raoult D. Serological differentiation of murine typhus and epidemic typhus using cross-adsorption and Western blotting. Clin Diagn Lab Immunol. 2000 July; 7(4):612-6.

11. La Scola B, Raoult D. Laboratory diagnosis of rickettsioses: current approaches to diagnosis of old and new rickettsial diseases. J Clin Microbiol. 1997 November; 35(11): 2715-27. Review.
12. Weil E., and A. Felix. 1916. Zur serologischen Diagnose des Fleckfiebers. Wien. Klin. Wochenschr. 29:33-35.
13. Ormsbee R, Peacock M, Philip R, Casper E, Plorde J, Gabre-Kidan T, Wright L. Serologic diagnosis of epidemic typhus fever. Am J. Epidemiol. 1977 March; 105(3):261-71.
14. Shepard C C, Redus M A, Tzianabos T, Warfield D T. Recent experience with the complement fixation test in the laboratory diagnosis of rickettsial diseases in the United States. J Clin Microbiol. 1976 September; 4(3):277-83.
15. Philip, R N, Casper E A, Ormsbee R A, Peacock M G, Burgdorfer W. Microimmunofluorescence test for the serological study of Rocky mountain spotted fever and typhus. J. Clin Microbiol. 3:51-61.
16. Shirai A, Dietel J W, Osterman J V. Indirect hemagglutination test for human antibody to typhus and spotted fever group rickettsiae. J Clin Microbiol. 1975 November; 2(5): 430-7.
17. Eremeeva, M E., N M. Balayeva, D. Raoult. Serological response of patients suffering from primary and recrudescent typhus: comparison of complement fixation reaction, Weil-Felix test, microimmunofluorescence, and immunoblotting. Clin. Diagn. Lab. Immunol. 1994, 1:318-324.
18. Kelly D J, Chan C T, Paxton H, et al. Comparative evaluation of a commercial enzyme immunoassay for the detection of human antibody to *Rickettsia typhi*. Clin Diagn Lab Immunol 1995; 2:356-60.
19. Jiang J, Temenak J J, Richards A L. Real-time PCR duplex assay for *Rickettsia prowazekii* and *Borrelia recurrentis*. Ann NY Acad. Sci. 2003 June; 990:302-10.
20. Kodama K, Senba T, Yamauchi H, Chikahira Y, Katayama T, Furuya Y, Fujita H, Yamamoto S. Fulminant Japanese spotted fever definitively diagnosed by the polymerase chain reaction method. J Infect Chemother. 2002 September; 8(3):266-8.
21. Palmer, E L., M L. Martin, and L. Mallavia. Ultrastructure of the surface of *Rickettsia prowazekii* and *Rickettsia akari*. Appl. Microbiol. 1974, 28:713-716.
22. Ching, W M., M. Carl, and G A. Dasch. Mapping of monoclonal antibody binding sites on CNBr fragments of the S-Layer protein antigens of *Rickettsia typhi* and *R. Prowazekii*. Mol. Immunol. 1992, 29:95-105.
23. Ching, W M., G A. Dasch, M. Carl and M E. Dobson. Structural analyses of the 120 Kda serotyupe protein antigens (SPAs) of typhus group rickettsiae: comparison with other S-layer proteins. Anna. N.Y. Acad. Sci. 1990, 590: 334-351.
24. Dasch, G A. Isolation of species-specific protein antigens of *Rickettsia typhi* and *Rickettsia prowazekii* for immunodiagnosis and immnuoprophylzxis. J. Clin. Microbiol. 1981, 14:333-341.
25. Dasch. G A., J R. Samms, and J C. Williams. Partial purification and characterization of the major species-specific protein antigens of *Rickettsia typhi* and *Rickettsia prowazekii* identified by rocket immunoelectrophoresis. Infect. Immun. 1981, 31:276-288.
26. Bourgeois, A L., and G A. Dasch. The species-specific surface protein antigens of *Rickettsia typhi*: immunogenicity and protective efficacy in guinea pigs. P. 71-80. In W. Burgdorfer and R L. Anacker (ed), *Rickettsia* and rickettsial diseases. Academic Press, New York.
27. Carl. M., and G A. Dasch. The importance of crystalline surface layer protein antigens of rickettsiae in T cell immunity. J. Autoimmun, 1989, 2:81-91.
28. Dasch, G A., and A L. Bourgeois. Antigens of the typhus group of rickettsiae: importance of the species-specific surface protein antigens in eliciting immunity, p 61-70. In W. Burgdorfer and R L. Anacker (ed), *Rickettsia* and rickettsial diseases. Academic Press, New York.
29. Dasch. G A., J P. Burans, M E. Dobson, F M. Rollwagen, and J. Misiti. Approaches to the subunit vaccines against the typhus rickettsiae, *Rickettsia typhi* and *Rickettsia prowazekii*, 251-256. In D. Schlessinger (ed), Microbiology-1984, American Society for Microbiology, Washington, D.C.
30. Ching, W M., H. Wang, J. Davis, and G A. Dasch. Amino acid analysis and multiple methylation of lysine residues in the surface protein antigen of *Rickettsia prowazekii*, p. 307-14. In R H. Angeletti (ed), Techniques in protein chemistry IV. Academic Press, San Diego.
31. Ching W M, Ni Y S, Kaplan H, Zhang Z, and Dasch G A (1997). Chemical methylation of *E. coli* expressed *Rickettsia typhi* protein increases its seroreactivity. Thirteenth Sesqui-Annual Meeting of American Society for Rickettsiology, Champion, Pa. abstract #40.
32. Chao C C, Wu S L, and Ching W M. Using LC-MS with De novo Software to Fully Characterize the Multiple Methylations of Lysine Residues in a Recombinant Fragment of an Outer Membrane Protein from a Virulent Strain of *Rickettsia prowazekii*. Biochimica
33. Ching W M, Zhang Z, Dasch G A, and Olson J G. Improved diagnosis of typhus rickettsiae using a chemically methylated recombinant s-layer protein fragment. Amer. Soc. Biochem. & Mole. Biol./Amer. Soc. Pham. & Exper. Therap. 2000. Boston, Mass. abstract #463.

What is claimed is:

1. A method of detecting *R. typhi* infection comprising the steps:

a. exposing a primary OmpB reagent to patient sera, wherein said primary OmpB reagent is Fragment A consisting of amino acid sequence of SEQ ID NO:2 encoded by the nucleotide sequence of SEQ ID NO:1 or Fragment K consisting of amino acid sequence of SEQ ID NO:4 encoded by the nucleotide sequence of SEO ID NO:3;

b. measuring bound antibody.

2. The method of claim 1, wherein said primary OmpB reagent is immobilized prior to exposure to patient sera.

3. The method of claim 1, comprising the additional step of also exposing to said patient sera to OmpB antigens selected from the group consisting of Fragment A consisting of amino acid sequence of SEQ ID NO: 2 encoded by the nucleotide sequence of SEQ ID NO:1, and Fragment K consisting of amino acid sequence of SEQ ID NO:4 encoded by the nucleotide sequence of SEQ ID NO:3, wherein said additional antigens are different from the primary antigen.

4. The method of claim 2, comprising the additional step of immobilizing additional OmpB antigens selected from the group consisting of Fragment A consisting of in amino acid sequence of SEQ ID NO: 2 encoded by the nucleotide sequence of SEQ ID NO:1 and Fragment K consisting of amino acid sequence of SEQ ID NO:4 encoded by the nucleotide sequence of SEQ ID NO:3, wherein said additional antigens are different from the primary antigen.

5. The method of claim 1, wherein said Fragment A is methylated or unmethylated.

* * * * *